United States Patent
Flury et al.

(10) Patent No.: US 9,505,916 B2
(45) Date of Patent: Nov. 29, 2016

(54) GEL-LIKE MASS COMPRISING NATURAL OR SYNTHETIC POLYMERS AND METHOD FOR PRODUCING THE GEL-LIKE MASS

(71) Applicant: JOKER AG, Kerzers (CH)

(72) Inventors: Meinrad Flury, Kerzers (CH); Benjamin Tak Kwong Lee, Hong Kong (CN); Pei Li, Hong Kong (CN); Edmond Ho Kin Man, Hong Kong (CN)

(73) Assignee: Polygum Technologies Ltd, Hong Kong (CN)

( * ) Notice: Subject to any disclaimer, the term of this patent is extended or adjusted under 35 U.S.C. 154(b) by 0 days.

(21) Appl. No.: 14/397,437

(22) PCT Filed: Apr. 18, 2013

(86) PCT No.: PCT/EP2013/058101
§ 371 (c)(1),
(2) Date: Oct. 27, 2014

(87) PCT Pub. No.: WO2013/160190
PCT Pub. Date: Oct. 31, 2013

(65) Prior Publication Data
US 2015/0125541 A1    May 7, 2015

(30) Foreign Application Priority Data

Apr. 25, 2012 (CH) .................................. 565/12

(51) Int. Cl.

| | | |
|---|---|---|
| C08L 5/00 | (2006.01) |
| C08B 37/00 | (2006.01) |
| C08J 3/075 | (2006.01) |
| C08J 3/24 | (2006.01) |
| A61K 47/36 | (2006.01) |
| A61K 9/70 | (2006.01) |
| A61K 9/10 | (2006.01) |
| A61K 31/618 | (2006.01) |
| C08K 3/28 | (2006.01) |
| C08K 5/053 | (2006.01) |
| C08K 5/134 | (2006.01) |
| C08K 5/29 | (2006.01) |
| C08K 5/3445 | (2006.01) |

(52) U.S. Cl.
CPC . *C08L 5/00* (2013.01); *A61K 9/10* (2013.01); *A61K 9/7007* (2013.01); *A61K 31/618* (2013.01); *A61K 47/36* (2013.01); *C08B 37/0087* (2013.01); *C08B 37/0096* (2013.01); *C08J 3/075* (2013.01); *C08J 3/242* (2013.01); *C08J 3/246* (2013.01); *C08K 3/28* (2013.01); *C08K 5/053* (2013.01); *C08K 5/134* (2013.01); *C08K 5/29* (2013.01); *C08K 5/3445* (2013.01); *C08J 2305/00* (2013.01)

(58) Field of Classification Search
CPC ...... C08L 9/06; C08B 37/0096; C08J 3/075; A61K 47/36
USPC ............ 525/55; 156/110; 424/499; 514/161; 524/105; 534/195
See application file for complete search history.

(56) References Cited

U.S. PATENT DOCUMENTS

| | | | |
|---|---|---|---|
| 5,756,273 A | 5/1998 | Wang et al. | |
| 6,359,032 B1* | 3/2002 | Kuwahara | A61K 8/736 523/201 |
| 2001/0053803 A1 | 12/2001 | Kuwahara et al. | |
| 2004/0045094 A1* | 3/2004 | Dietrich | C11D 3/042 8/115.51 |
| 2006/0116473 A1 | 6/2006 | Castner et al. | |

FOREIGN PATENT DOCUMENTS

WO    WO 02/055642 A2    7/2002

OTHER PUBLICATIONS

Poole et al; Title: Development and evaluation of topical formulation containing solid lipid nanoparticles of vitamin A. AAPS PharmSciTech. vol. 7(4):91, published Nov. 17, 2006.*

* cited by examiner

*Primary Examiner* — Johann R Richter
*Assistant Examiner* — Yanzhi Zhang
(74) *Attorney, Agent, or Firm* — Pauley Erickson & Kottis

(57) ABSTRACT

In a gel-like mass having natural or synthetic polymers, preferably polygalactomannans, at least one cross-linking agent and further ingredients, according to this invention that the at least one cross-linking agent is of amphiphilic core-shell nanoparticles. This invention further refers to a method for producing a gel-like mass, a composition for producing a gel-like mass comprising natural or synthetic polymers, preferably polygalactomannans and amphiphilic core-shell nanoparticles and the use of a gel-like mass as drug delivery system for topical medication.

26 Claims, 3 Drawing Sheets

0.75%  1.00%

1.50%  1.75%

2.00%  2.50%

GEL-LIKE MASS COMPRISING NATURAL OR SYNTHETIC POLYMERS AND METHOD FOR PRODUCING THE GEL-LIKE MASS

BACKGROUND OF THE INVENTION

Field of the Invention

This invention is related to a gel-like mass having natural or synthetic polymers, preferably polygalactomannans, at least one cross-linking agent and further ingredients. It further relates to a method for producing a gel-like mass, a composition for producing a gel-like mass and the use of a gel-like mass.

Discussion of Related Art

Under the name Slimy and Mega Slimy gel-like toy products are known, which are based on natural polygalactomannans or synthetic polymers. The products are formulated in a manner such that a soft, easily deformable slightly sticky gel-like mass results.

PCT Reference WO 02/055642 describes a gel-like mass also based on natural polygalctomannans or synthetic polymers for removing solid particles from surfaces. The gel-like mass is easily deformable and adapts to every contour of a surface. Due to its consistency, its constitution and its chemical structure, the gel-like mass may be cut up or reduced in size and may also "grow together" again.

Guar gum, also called guaran, is a family of polygalactomannans, polysaccharides composed of galctose and mannose units. It is often used as an emulsifier, a thickener, a stabilizer, and is approved for use in a wide range of food, cosmetics, and pharmaceuticals.

To obtain the above mentioned gel-like mass, the polygalctomannans are cross-linked with boron-containing compounds, such as Borax or boric acid, resulting in a gel-like mass with a boron content of more than 0.05 percent by weight (or 500 ppm) in the final compound/mass.

However, while boron has found its uses in many products, the use of it at high concentrations has raised some concerns on human health. The European Commission poses a new regulation (Directive 2009/48/EC of the European Parliament and of the Council of 18 Jun. 2009 on the safety of toys) on limiting migration boron (leachable) from liquid or sticky (toys) products to no more than 300 mg/kg (0.03%). Therefore, there is an incentive to generally reduce the boron content in these products.

SUMMARY OF THE INVENTION

It is one objective of this invention to provide a gel-like mass comprising cross-linked natural or synthetic polymers with reduced health risk due to reduced leachable boron content. The gel-like mass should nevertheless show the desired soft and easily deformable properties with good mechanical and elongation strength. After cutting it apart it should be able to "grow together" and form a cohesive mass again.

The above objective of this invention is achieved by a gel-like mass according to this specification and the claims. Thus according to this invention, with the gel-like mass comprising natural or synthetic polymers, preferably polygalctomannans, at least one cross-linking agent and further ingredients, at least one cross-linking agent comprises amphiphilic core-shell nanoparticles. These amphiphilic core-shell nanoparticles serve as a cross-linking agent to form a stable gel-like mass with the polymers via various types of interactions, such as hydrogen bonding, interpenetration network, electrostatic and/or complexation interactions, and can at least partially replace boron as the cross-linking agent. The gel-like mass according to this invention has a significantly reduced content of boron and still shows the desired mechanical characteristics of several primary parameters of hardness, cohesiveness, elasticity, and adhesiveness, and into the secondary (or derived) parameters of fracturability (brittleness), and gumminess.

Another effect of the nanoparticles is that they optimize the suspension of the polymers units and thereby increase the accessibility for boron to cross-link the polymer units, in the case that boron is used as an additional cross-linking agent.

The gel-like mass according to this invention is suitable for entertainment, therapeutical, medicinial, cosmetic, industrial and agricultural use, such as because of its reduced boron content. It can be used as a drug delivery system platform to deliver active pharmaceutical ingredients or act as a media for cosmetics, such as for topical administration of medicine or time-controlled release of the active ingredients.

In one embodiment of this invention, the core of the amphiphilic core-shell nanoparticles comprises hydrophobic vinylic grafted copolymers and hydrophobic vinylic polymer, and the shell of the amphiphilic core-shell nanoparticles to which the hydrophobic vinylic polymer is grafted is a hydrophilic, nitrogen-containing polymer.

In a further preferred embodiment of this invention, the core of the amphiphilic core-shell nanoparticles comprises poly (methyl methacrylate) (PMMA) and/or the shell of the amphiphilic core-shell nanoparticles comprises chitosan (CTS).

Alternatively, the nanoparticles comprise a poly (N-isopropyl acrylamide) core with a chitosan shell (PNIPAm-CTS) or a PMMA core with a quaternized chitosan shell (PMMA-qCTS).

In all embodiments of this invention, the gel-like mass preferably comprises 0.5 to 5%, preferably 0.5 to 3%, by weight of amphiphilic core-shell nanoparticles. The average diameter of the amphiphilic core-shell nanoparticles is preferably in the range of 100 to 1000 nm, more preferably between 100 and 500, mostly preferred between 150 and 250 nm.

Preferably, the gel-like mass has a viscosity of 5'000 to 250'000 mPa·s, preferably between 120'000 and 200'000 mPa·s and mostly preferred about 150'000 mPa·s. The viscosity was measured with a Brookfield DVII+ viscometer at 22.5° C. using a S64 Spindle.

In all embodiments of this invention, guar gum, also called guaran, is preferably used as polygalactomannans. Preferably, the guar is hydroxypropyl guar (HPG) or carboxymehtylated guar (CMG) or a combination of both guars. The gel-like mass may comprise preservatives against mold and bacterial growth, such as (but not limited to) methyl paraben, propyl paraben, Germal II, silver nitrate, PHMB, BTC, chlorhexidine and combinations thereof. Additionally, the gel-like mass may further comprise glycerin to adjust stickiness and the water retention ability.

Stickiness in the sense of this invention is the property of sticking to a surface. As human skin is hydrophilic in nature, if the surface of the gel-like mass is too hydrophilic, it will cause a sticky hand feel. Therefore, a reduction in stickiness may be preferred.

In a further preferred embodiment of this invention, the gel-like mass further comprises an active compound or ingredient, preferably a drug or medicine, stabilized by the amphiphilic core-shell nanoparticles. The gel-like mass then allows for a slow drug or medicine release profiling, which is particularly suitable for topical administration of drugs or medicines to the skin. Such a gel-like mass is also suitable for topical administration for active compounds or ingredients of cosmetics. The active compound or ingredient is preferably selected from the group of (but not limited to) methyl salicylate; glycol salicylate; menthol; camphor; trolamine salicylate; capsaicin, ibuprofen, diclofenac sodium; turpentine oil; eucalyptus oil; and peppermint oil.

A further aspect of this invention relates to a method for producing a gel-like mass according to one of the embodiments described above, comprising the steps of (i) providing an aqueous solution comprising natural or synthetic polymers, preferably polygalactomannans; (ii) adding amphiphilic core-shell nanoparticles, preferably as a suspension, while continuously stirring the aqueous solution to obtain a homogenous suspension; and (iii) standing the suspension mixture of natural or synthetic polymers, preferably natural or synthetic polygalactomannans, and the amphiphilic core-shell nanoparticles for an amount of time, preferably several hours, to obtain the gel-like mass. During the standing cross-linking of the natural or synthetic polymers, preferably polygalactomannans, with the amphiphilic core-shell nanoparticles will occur. Preferably, the stirring is performed in a homogenizer or by using a mechanical stirrer at a stirring rate between 300 and 700 rpm.

In a further embodiment of the method of this invention, the polymers, preferably polygalactomannans, are mixed with preservatives against mold and bacterial growth, such as (but not limited to) methyl paraben, propyl paraben, Germal II, silver nitrate, PHMB, BTC, chlorhexidine and combinations thereof before step (i).

Preferably, 2-7% glycerin, more preferably 3.5 to 5.6%, is added to the suspension between step (ii) and (iii) while continuously stirring the suspension, to adjust stickiness and the water retention ability of the gel-like mass.

In a further preferred embodiment of this invention, the pH of the suspension is adjusted to 6.8 to 8.0, preferably 7.0 to 7.6, before step (iii).

If needed, small amounts of boric acid or borax can be mixed with the natural or synthetic polymers, preferably polygalactomannans, before step (i) to obtain a final boron concentration in the gel-like mass of less than 0.017% by weight, to support the cross-linking by the amphiphilic core-shell nanoparticles.

Another aspect of this invention relates to the composition for producing a gel-like mass according to this invention. The composition comprising in % by weight: 3-7% natural or synthetic polymers, preferably polygalactomannans, 0.5-3.0% amphiphilic core-shell nanoparticles, 2-7% glycerin, 0-1% preservatives, and 0-0.017% boron. Water ($H_2O$) is added to obtain a total of 100% by weight of gel-like mass.

In another embodiment of this invention, the composition comprises more than 65% by weight, preferably 82% by weight, more preferably 86% by weight, of water. Preferably, the polygalactomannan is guar, preferably hydroxypropyl guar (HPG) and/or carboxymehtylated guar (CMG), more preferably a mixture of hydroxypropyl guar (HPG) and carboxymehtylated guar (CMG) in a HPG/CMG ratio of 1:1 to 10:1 (weight ratio), preferably 9:1. The amount of nanoparticle is preferably 0.75 to 2.5% by weight, more preferably 1.25% by weight. Further ingredients selected from aluminium chloride, barium sulfate, calcium carbonate, sodium silicate, pigments, colorants, calcium sulfate, sodium hydrogen phosphate, sodium hydrogen carbonate, potassium sorbate, calcium chloride, hydrochloric acid, sodium hydroxide and potassium hydroxide can be added.

In a further embodiment of this invention, the composition comprises an active compound or ingredient, preferably a drug or medicine or an active compound or ingredient used for cosmetics, stabilized and encapsulated by the amphiphilic core-shell nanoparticles.

Another aspect of this invention is the use of a gel-like mass according to this invention as a drug delivery system for topical medication to manage, for example, muscle ache and joint pain and to enhance rehabilitation. Therefore, a drug, for example, methyl salicylate or diclofenac and core-shell nanoparticles can be homogenized to obtain a nanoparticle-stabilized drug emulsion. The emulsion can then be used for producing the gel-like mass according to this invention. The gel-like mass according to this invention can also be used as delivery system for topical administration of cosmetic compounds.

The gel-like mass according to this invention with its reduced boron content is further suitable for entertainment, therapeutic, medicinal, cosmetic, industrial and agricultural use.

The gel-like mass according to this invention can be used as ultrasound coupling medium for use in medical diagnostics. When used as coupling medium the gel-like mass preferably comprises at least 90% by weight of water and is preferably semi-liquid. It can be extracted into a 1/10 mm thick film and can withstand a pressure of up to 30 kp without tearing. Such a gel-like mass can adapt to the surface of the skin without causing any significant air pockets, which would compromise the quality of a sonogram. The gel-like mass has preferably a particularly slow-flowing cohesive consistency and is "visco-elastic", such that it will not leave behind any residue when removed from the skin.

The coupling medium may be extracted into a thin and ductile film, and it may be cut and reduced into any sizes and different pieces of the medium may be remolded into one collective piece of medium.

The natural or synthetic polymer of the coupling medium may be a polysaccharide, preferably a galactomannan, such as guar seed meal, carob seed meal; polyvinyl alcohol (PVA) or combinations thereof.

Galactomannan is a group of vegetable fibrils that are found as reserve carbohydrates mainly in the seeds of many leguminous plants. Guar gum is the common term for the ground endosperm of the guar bean, such as Cyamopsistetragonoloba L. or Cyamopsis psoraloides DC. The vegetable macromolecules contain polymannose main chains with galactose side chains. The application possibilities of galactomannans in the field of general technological processes are very versatile. As a trade product, these hydrocolloids are mainly applied as gelling and thickening agents. The galactomannans together with amphiphiliccore-shell nanoparticles and other cross-linking agents as described above form hardly soluble complexes, which may also be used as an ultrasound coupling medium.

Polyvinyl alcohol (PVA) is commonly used for the manufacture of pharmaceutical emulsions, ointments, and cosmetics, such as facial masks and skin protection ointments. Since polyvinyl alcohols are polymers of vinyl alcohol, they cannot exist in free form. Thus, in embodiments where a polyvinyl alcohol is used as a base substance to formulate the inventive ultrasound coupling medium, the formulation process involves the hydrolysis (saponification) of polyvinyl acetate. Also, the polyvinyl alcohols used to formulate this invention generally meet the legal requirements with respect to the degree of purity. The regularly arranged hydroxyl groups of the polyvinyl alcohol chain can also form chemically stable complex compounds or associate with the above described amphiphilic core-shell nanoparticles and other cross-linking agents.

The gel-like mass according to this invention can further be used for wound covering. When used as wound cover the gel-like mass preferably comprises antiseptic and/or pain relieving substances. These active substances can be stabilized and encapsulated by the amphiphilic nanoparticles as described above. Additionally, the gel-like mass can comprise cell-regenerating substances to promote healing of the wound covered by the gel-like mass. The gel-like mass can also contain haemostatic substances, which are advantageous when using the gel-like mass as a wound cover during an operation.

The gel-like mass according to this invention comprising the amphiphilic core-shell nanoparticles has among others the following advantages:

Amphiphilic core-shell particles can act as a crosslinker to crosslink the polymer and form gel-like mass. Thus the amount of undesirable boron based crosslinker can be considerably reduced.

Amphiphilic core-shell particles are capable of encapsulating water-insoluble drug molecules so that the oily drugs become compatible with the hydrophilic guargum.

Amphiphilic core-shell particles also can enhance mechanical property of the gel due to the presence of hard PMMA cores.

BRIEF DESCRIPTION OF THE DRAWINGS

This invention is described in greater detail below in view of embodiments that are illustrated in the figures, wherein.

DETAILED DESCRIPTION OF THE INVENTION

Synthesis and Characterization of Core-Shell Nanoparticles:

Three types of core-shell nanoparticles including PMMA-CTS, PNIPAm-CTS, PMMA-qCTS, have been synthesized according to a previously developed graft copolymerization method (Li P, Zhu J, Harris F W. Amphiphilic core-shell latexes. U.S. Pat. No. 6,573,313 (2003); Li P, Zhu J, Sunintaboon P, Harris F W. *New route to amphiphilic core-shell polymer nanospheres: Graft copolymerization of methyl methacrylate from water-soluble polymer chains containing amino groups. Langmuir.* 2002; 18(22):8641-6. Leung M F, Zhu J, Harris F W, Li P. *New route to smart core-shell polymeric microgels: synthesis and properties. Macromol Rapid Commun.* 2004; 25(21):1819-23.). Chitosan is used as a shell because it is a nontoxic, biocompatible and biodegradable natural polymer with inherent antibacterial properties. Table 1 shows the properties of the core-shell nanoparticles produced. All of the nanoparticles synthesized have high monomer conversions (>90%), which means that 90% monomer has been converted to the polymer after reaction. To remove the residual monomers, the nanoparticles were further purified using rotary evaporation. PMMA-CTS core-shell nanoparticles have an average diameter ranging from 200 to 400 nm, while PNIPAm-CTS microgels have a bigger size with an average size ranging from 400 to 800 nm. PMMA-qCTS nanoparticles have an average size ranging from 200 to 400 nm. Particle size measurements also indicated that all the core-shell nanoparticles produced have narrow size distribution, as indicated by their low PDI value (<0.15). All of the nanoparticles were purified through repeated centrifugation and re-dispersion cycle until the conductivity of the supernatants is similar to deionized water. Except for PMMA-qCTS nanoparticles which were dispersed in water, PMMA-CTS nanoparticles and PNIPAm-CTS microgels were dispersed in an acidic solution (pH~5) for subsequent use.

TABLE 1

Properties of core-shell nanoparticles synthesized.

| Types of core-shell nanoparticles | Monomer conv. (%) | Dispersion pH after purification | $D_h$ (nm) | PDI* |
|---|---|---|---|---|
| PMMA-CTS | 92-99 | 4-6 | 200-400 | <0.15 |
| PNIPAm-CTS | 90-99 | 4-6 | 400-800 | <0.15 |
| PMMA-qCTS | 90-99 | 6-8 | 200-400 | <0.15 |

*The PDI value indicates the polydispersity of the particles. If the PDI value is lower than 0.15, the particles are considered to have nearly uniform diameter with narrow size distribution according to the specification from the supplier.
*The PDI value indicates the polydispersity of the particles.

Preparation of Gel-Like Mass:

Samples were prepared by mixing HPG or a mixture of HPG and CMG with boric acid or borax and subsequently dissolving in water using a homogenizer. Nanoparticles were added to the homogenized solution. The resulting mixture was placed in a water bath at 20-30° C. for 24 hours for cross-linking.

Figure 1A:
FIG. 1 shows photographs of the 0.017% boron-crosslinked HPG/CMG gel-like mass with addition of 1% PMMA-CTS nanoparticles (a); and without addition of nanoparticles (b)
Figure 1B:

FIG. 1(a) shows a gel-like mass with 0.017% boron-crosslinked HPG/CMG (5%) with 1% PMMA-CTS nanoparticles. The sample shows good elongation strength and elastic strength. FIG. 1(b) shows a gel-like mass with 0.017% boron-crosslinked guar (with 5% guar content) without nanoparticles. Samples containing nanoparticles exhibit good elongation strength. In comparison, samples without addition of nanoparticles have relatively poor elongation ability. Furthermore, it is too sticky and soft. The good elongation strength of the gel-like mass containing nanoparticles may be contributed to the presence of both hydrogen bonding and electrostatic complexation between nanoparticles and guar.

TABLE 2

Samples with and without nanoparticles.
All numbers given in % are by weight.

| | Sample of FIG. 1(a) | Sample of FIG. 1(b) |
|---|---|---|
| Modified guar (HPG, CMG) | 5% | 5% |
| Boron | 0.017% | 0.017% |
| Nanoparticles | 1% | 0% |
| Other ingredients | 7.47% | 7.47% |
| Water | 87.43% | 88.43% |

In order to obtain the desired gel-like mass with low boron content, success has been achieved by replacing most of the boron of the reference sample (including in percent by weight: HPG 4.8%, glycerin 7.2%, boron 0.067% and water 71.6%; not including nanoparticles) with amphiphilic core-shell nanoparticles (NP) having a core comprising poly (methyl methacrylate) (PMMA) and a shell comprising chitosan (CTS). The nanoparticles served as additional cross linking agents and formed a stable gel with guar gum via various types of interactions (hydrogen bonding, interpenetration network, electrostatic and boron-complexation interactions). The nanoparticles can also serve as encapsulating agents of medicine for slow releasing. Compared to gel-like mass of the reference sample, the boron content could be reduced from the current 0.067% to 0.017% while still achieving a gel-like mass with acceptable physical attributes in terms of its mechanical/elongation strength and hand feel properties.

Table 3 shows the effect of various contents of PMMA-CTS nanoparticles on the 0.017% boron-crosslinked 4.8% HPG/0.5% CMG gel-like mass. The "*" indicates relative stickiness of the gel-like mass, where "*" is equivalent to the stickiness of the reference sample. The increase in number of "*" means increase in stickiness. The "+" indicates relative elongation strength of the gel-like mass after storage for 7 days, where "+++++" is equivalent to the elongation strength of the reference sample. The "x" indicates relative mechanical strength of the hydrogels, where "xxxx" is equivalent to the mechanical strength of the reference sample.

TABLE 3

Effect of various contents of PMMA-CTS nanoparticles on the 0.017% boron-crosslinked 4.8% HPG/0.5% CMG gel-like mass.

| % by weight of PMMA-CTS nanoparticles | Stickiness | Mechanical strength | Elongation strength |
| --- | --- | --- | --- |
| 0.75% | **** | xxxx | ++++ |
| 1.0% | **** | xxxxx | ++++ |
| 1.5% | *** | xxxxx | +++++ |
| 1.75% | *** | xxxxxxx | +++++ |
| 2.0% | *** | xxxxxxx | +++++ |
| 2.5% | * | xxxxxxx | ++++ |

Figure 2:
FIG. 2 shows photographs of the gel-like mass according to this invention containing various PMMA-CTS nanoparticle contents: 0.75%; 1.0%; 1.5%; 1.75%; 2.0%; 2.5%.
Figure 2:
Figure 2:
Figure 2:
Figure 2:
Figure 2:

FIG. 2 shows photographs of the samples of Table 3 of a gel-like mass according to this invention containing various PMMA-CTS nanoparticle contents: 0.75%; 1.0%; 1.5%; 1.75%; 2.0%; 2.5%.

Increasing the nanoparticle concentration up to 2.5% significantly improved the stickiness of the gel-like masses. Furthermore, it also significantly enhanced mechanical strength, but without affecting the elongation strength. The 2.5% PMMA-CTS/4.8% HPG/0.5% CMG gel-like mass has even better mechanical strength than the reference sample.

Figure 3:
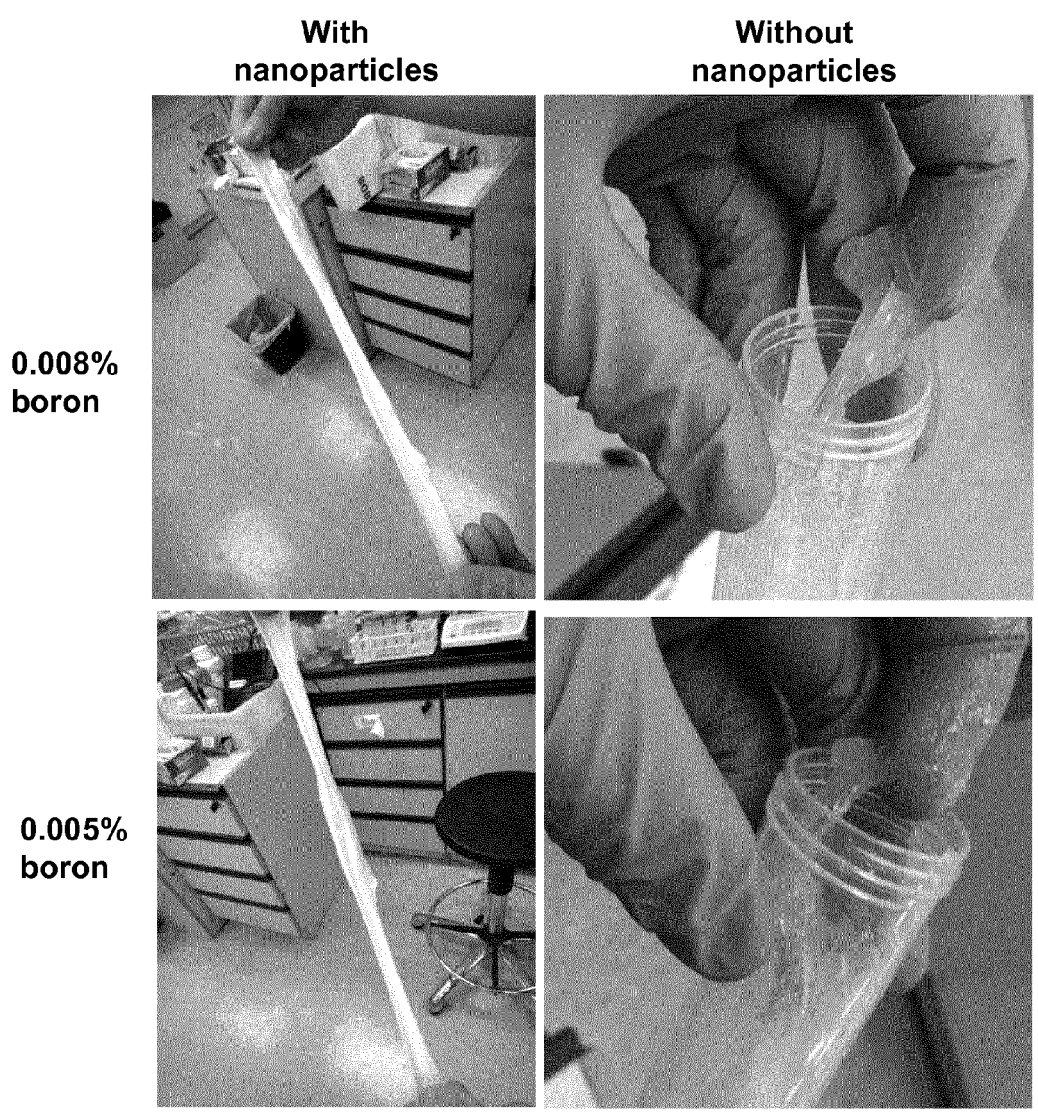
FIG. 3 shows photographs of the 5.3% HPG/CMG gel-like mass with a boron crosslinking percentage of (a) 0.008% (left image: with 2.5% PMMA-CTS nanoparticles; right image: without nanoparticles) and (b) 0.005% (left image: with 2.5% PMMA-CTS nanoparticles; right image: without nanoparticles).

An attempt to further reduce boron content in the gel-like mass has been made. FIG. 3 shows photographs of the 5.3% HPG/CMG gel-like mass with boron crosslinking of (a) 0.008% by weight of boron (left image: with 2.5% PMMA-CTS nanoparticles; right image: without nanoparticles) and (b) 0.005% by weight of boron (left image: with 2.5% PMMA-CTS nanoparticles; right image: without nanoparticles). The photographs show that the boron content of the gel-like mass can be reduced to as low as 0.005% to 0.008% by weight and still show a gel-like mass with much reduced stickiness and better elongations strength compared to the gel-like mass without nanoparticles.

The general feasibility to use a gel-like mass according to this invention as a drug delivery vehicle for topical medication, e.g. to manage muscle ache and joint pain, has been shown. Therefore, a nanoparticle-stabilized methyl salicylate emulsion was prepared by homogenizing a PMMA-CTS dispersion with (but not limited to) methyl salicylate. Methyl salicylate, as an example, is proposed as an active ingredient for pain relief. The dispersion was subsequently used to produce a stable gel-like mass.

The following table gives a range of compositions of a gel-like mass for the use as drug delivery vehicle for topical medication (all numbers given in % by weight). The gel-like mass comprises methyl salicylate as an example of the active compound:

| Ingredient | Composition (% by weight) |
| --- | --- |
| Active compound (i.e. methyl salicylate) | 5-20 |
| Polygalactomannan (i.e. HPG and CMG) | 5.5-10 |
| Nanoparticles (i.e. PMMA-CTS) | 0.5-5 |
| Glycerin | 5.5-5.6 |
| Boron* | 0.0017-0.0255 |
| Menthol | 3-10 |
| Camphor | 0-5 |
| Cremophor | 2-5 |
| Preservatives | 0.3-1.5 |
| Zinc oxides | 0.1-0.5 |
| Zinc sulphate (ZnSO4·7H2O) | 0.5 |
| Fragrance | 0.1-0.6 |
| Water (i.e. DDI H2O) | to obtain a total of 100 |

(*Boron content of boron-containing compounds, such as Borax or boric acid)

Examples for Gel-Like Mass of Polygalactomannan and PVA:

A gel-like mass used as ultrasound coupling medium can comprise at least one PVA with a hydrolysis degree (saponification degree) of at least 85 mole percent. Preferably, fully-hydrolyzed PVA (hydrolysis degree of at least 98 mole percent) is used. For example, the viscosity of the hydrolyzed PVA in a 4 percent aqueous solution (20[deg.] C.) is 30 mPa·s.

A good compatibility can be achieved by utilizing an alkylated galactomannan having a substitution degree D S of 0.2 to 0.6 (preferably hydroxypropyl-guar DS 0.3-0.5). The preferred viscosity of the hydroxypropyl guar in a 2 percent aqueous solution is 10,000-12,000 mPa·s. (Brookfield D VII+ viscometer at 22.5° C. using a S64 Spindle).

Alternatively, the gel-like mass comprises a hydroxyalkyl derivative. The hydroxyalkyl derivative may be manufactured by mixing a polysaccharide with an ethylene oxide or a propylene oxide in an alkaline medium.

One example comprises at least 90% by weight of water, and a mixture of about 1 to 5 percent by weight of galactomannan and about 0.3 to 5 percent by weight of PVA, having a pH-value of 6.5 to 8.5. For complex formation, 0.5 to 3% by weight of amphiphilic core-shell nanoparticles and 0 to 0.017% by weight of boron may be used.

The desired visco-elastic property is set on the basis of the mixing ratio of galactomanan and PVA, and by way of the addition of a suitable softening agent to achieve the interaction of the viscous and elastic components. Suitable softeners may be selected from the group consisting of: ethyl glycol, diethylene glycol, triethylene glycol, PEG, and glycerine. In one embodiment of the inventive ultrasound coupling medium, the desired "visco-elasticity" is set by way of the addition of 0.2 to 1.5 percent by weight of glycerine.

The following table gives a range of further compositions of a gel-like mass for use as ultrasound coupling mediums utilizing galactomannan (all numbers given in % by weight):

| Ingredient | Composition (% by weight) |
| --- | --- |
| Polygalactomannan (i.e. CMG) | 5-7 |
| Nanoparticles (i.e. PMMA-Chitosan) | 0.5-5 |
| Boron* | 0.0085-0.017 |
| Glycerin | 3.5 |
| Ethanol | 15-20 |
| Preservatives | 0.5-2.6 |
| Dipotassium hydrogen phosphate | 0.1-0.3 |
| Citric acid | 0.001-0.1 |
| Aluminum chloride | 0.1 |
| Other ingredients (e.g. colorants) | 0.37-0.9 |
| Water | to obtain a total of 100 |

(*Boron content of boron-containing compounds, such as Borax or boric acid)

The invention claimed is:

1. A gel-like mass comprising natural or synthetic polymers, at least one cross-linking agent for cross-linking the natural or synthetic polymers, 0-0.008 wt % boron and further ingredients, and the at least one cross-linking agent being an amphiphilic core-shell nanoparticle and the gel-like mass comprising 0.5 to 5% by weight of the amphiphilic core-shell nanoparticle.

2. The gel-like mass according to claim 1, wherein a core of the amphiphilic core-shell nanoparticle comprises hydrophobic vinylic grafted copolymers and hydrophobic vinylic polymers, and the shell of the amphiphilic core-shell nanoparticle to which the hydrophobic vinylic polymer is grafted comprises a hydrophilic, nitrogen-containing polymer.

3. The gel-like mass according to claim 2, wherein the core of the amphiphilic core-shell nanoparticles comprises poly(methyl methacrylate) (PMMA) and/or the shell of the amphiphilic core-shell nanoparticles comprises chitosan (CTS).

4. The gel-like mass according to claim 3, wherein an average diameter of the amphiphilic core-shell nanoparticles is in a range of 100 to 1000 nm.

5. The gel-like mass according to claim 4, wherein the gel-like mass has a viscosity of 5,000 to 250,000 mPa·s.

6. The gel-like mass according to claim 5, wherein the polymers comprise guar selected from hydroxypropyl guar (HPG) or carboxymethylated guar (CMG).

7. The gel-like mass according to claim 6, further comprising an active compound stabilized by the amphiphilic core-shell nanoparticle.

8. The gel-like mass according to claim 6, further comprising a drug or a medicine stabilized by the amphiphilic core-shell nanoparticle.

9. A method for producing a gel-like mass according to claim 1 comprising the steps of:
providing an aqueous solution comprising the natural or synthetic polymers;
(ii) adding the amphiphilic core-shell nanoparticles while continuously stirring the aqueous solution to obtain a homogenous suspension; and
(iii) standing the suspension mixture of natural or synthetic polymers and the amphiphilic core-shell nanoparticles for an amount of time to allow cross-linking of the natural or synthetic polymers with the amphiphilic core-shell particles to obtain the gel-like mass.

10. The gel-like mass according to claim 1, wherein the core of the amphiphilic core-shell nanoparticles comprises poly(methyl methacrylate) (PMMA) and/or the shell of the amphiphilic core-shell nanoparticles comprises chitosan (CTS).

11. The gel-like mass according to claim 1, wherein an average diameter of the amphiphilic core-shell nanoparticles is in a range of 100 to 1000 nm.

12. The gel-like mass according to claim 1, wherein the gel-like mass has a viscosity of 5,000 to 250,000 mPa·s.

13. The gel-like mass according to claim 1, wherein the polymers comprise guar selected from hydroxypropyl guar (HPG) or carboxymethylated guar (CMG).

14. The gel-like mass according to claim 1, further comprising a drug or a medicine stabilized by the amphiphilic core-shell nanoparticle.

15. The composition of claim 1 further comprising an active compound selected from the group of a drug compound, methyl salicylate, glycol salicylate, menthol, camphor, trolamine salicylate, capsaicin, ibuprofen, diclofenac, turpentine oil, eucalyptus oil and pepper-mint oil, wherein the active compound is stabilized and encapsulated by the amphiphilic core-shell nanoparticles.

16. The gel-like mass according to claim 1, wherein the natural or synthetic polymers comprise polygalactomannans.

17. The gel-like mass according to claim 1, wherein the gel-like mass comprises 0.5 to 3% by weight of the amphiphilic core-shell nanoparticle.

18. The gel-like mass according to claim 1, wherein an average diameter of the amphiphilic core-shell nanoparticles is between 150 and 250 nm.

19. A composition for producing a gel-like mass according to claim 1 comprising in % by weight:

| | |
| --- | --- |
| polygalactomannan | 3-7%, |
| amphiphilic core-shell nanoparticles | 0.5-5.0%, |
| glycerin | 2-7%, |
| preservatives | 0-1%, |
| boron | 0-0.008%, |
| and water (H$_2$O) to obtain a total of 100% by weight of a gel-like mass. | |

20. The composition of claim 19, comprising more than 65% by weight of water.

21. The composition of claim 19 wherein the polygalactomannan is guar.

22. The composition of claim 21 further comprising an active compound selected from the group of a drug compound, methyl salicylate, glycol salicylate, menthol, camphor, trolamine salicylate, capsaicin, ibuprofen, diclofenac, turpentine oil, eucalyptus oil and pepper-mint oil, wherein the active compound is stabilized and encapsulated by the amphiphilic core-shell nanoparticles.

23. The composition of claim 19, comprising more than 86% by weight of water.

24. The composition of claim 19 wherein the polygalactomannan is hydroxypropyl guar (HPG) and/or carboxymehtylated guar (CMG).

25. The composition of claim 19 wherein the polygalactomannan is a mixture of hydroxypropyl guar (HPG) and carboxymehtylated guar (CMG) in a HPG/CMG weight ratio of 1:1 to 10:1.

26. A gel-like mass comprising water, crosslinked polymers, and a cross-linking agent, wherein the cross-linking agent includes 0.005-0.008 wt % boron and amphiphilic core-shell nanoparticles, wherein the gel-like mass is 0.5 to 5%, by weight of the amphiphilic core-shell nanoparticles.

* * * * *